US005885559A

United States Patent [19]
Lee et al.

[11] Patent Number: 5,885,559
[45] Date of Patent: Mar. 23, 1999

[54] SOLID COSMETIC COMPOSITION CONTAINING HEXANEDIOL-BEHENYL BEESWAX AS GELLING AGENT

[75] Inventors: Wilson Lee, Bloomfield; Robert Bianchini, Belle Mead, both of N.J.

[73] Assignee: Colgate Palmolive Company, New York, N.Y.

[21] Appl. No.: 709,443

[22] Filed: Sep. 6, 1996

[51] Int. Cl.$^6$ .............................. A61K 7/32; A61K 7/38; A61K 7/00
[52] U.S. Cl. .............................. 424/65; 424/68; 424/400; 424/401
[58] Field of Search ................................ 424/65, 68, 400, 424/401

[56] References Cited

U.S. PATENT DOCUMENTS

| | | |
|---|---|---|
| 2,765,213 | 10/1956 | Beckman . |
| 4,331,653 | 5/1982 | Brown et al. . |
| 4,526,780 | 7/1985 | Marschner et al. . |
| 4,840,789 | 6/1989 | Orr et al. . |
| 4,853,214 | 8/1989 | Orr . |
| 4,937,069 | 6/1990 | Shin . |
| 4,948,584 | 8/1990 | Brand . |
| 5,019,375 | 5/1991 | Tanner et al. . |
| 5,069,897 | 12/1991 | Orr . |
| 5,102,656 | 4/1992 | Kasat . |
| 5,160,739 | 11/1992 | Kanga . |
| 5,531,986 | 7/1996 | Shevade et al. ........................... 424/68 |
| 5,541,148 | 7/1996 | Glock et al. ............................. 504/112 |

FOREIGN PATENT DOCUMENTS 2701395   8/1994   France .

*Primary Examiner*—Shelley A. Dodson
*Attorney, Agent, or Firm*—William I. Solomon; Rosemary M. Miano

[57] ABSTRACT

Disclosed is a solid (e.g., cream, such as semi-solid or soft solid) cosmetic composition containing an active cosmetic material (e.g., a deodorant active, an antiperspirant active, a sunscreen, an insect repellent and/or an anti-fungal agent), volatile (e.g., cyclomethicone) and linear chain (e.g., dimethicone and/or phenyl trimethicone) silicone materials, and at least one gelling agent. The at least one gelling agent includes hexanediol-behenyl beeswax, and is included in the composition in an amount sufficient to provide the solid composition. By incorporating the hexanediol-behenyl beeswax as a gelling agent, conventional gelling agents such as fatty alcohols and hydrogenated castor oil need not be incorporated in the composition. When an antiperspirant active material is incorporated in the solid composition containing hexanediol-behenyl beeswax as a gelling agent, a solid antiperspirant composition that is efficacious and leaves no visible (white) residue, can be achieved.

5 Claims, No Drawings

SOLID COSMETIC COMPOSITION CONTAINING HEXANEDIOL-BEHENYL BEESWAX AS GELLING AGENT

BACKGROUND OF THE INVENTION

The present invention is directed to a solid cosmetic composition which leaves substantially no visible (white) residue on the skin, which is stable and substantially anhydrous, and which is efficacious. In particular, the present invention is directed to a solid (for example, a cream) cosmetic composition containing active cosmetic material (for example, selected from deodorant active materials, sunscreen materials, insect repellents and antifungal agents), which leaves substantially no visible residue on the skin and which is efficacious.

The present invention especially relates to an antiperspirant cream composition containing an antiperspirant active agent (an antiperspirant active metal salt, such as an antiperspirant active aluminum salt and/or an antiperspirant active aluminum-zirconium salt) and to a deodorant cream composition containing a deodorant active agent ( for example, a bacteriostat, such as Triclosan), which exhibit the aforementioned properties.

Antiperspirant products are well known in the art. Antiperspirant products have appeared in the market in various dosage forms, such as sticks, gels, roll-ons, aerosols and creams. Of these dosage forms, various sticks, gels and creams are constituted by a liquid base material solidified by a solidifying agent (for example, a gelling agent), and these fall within solid cosmetic composition according to the present invention. Generally, the dosage forms include a solution of the active ingredient in a suitable solvent, a suspension of the active ingredient in a non-active solvent, or a multi-phasic dispersion or emulsion in which the active ingredient is dispersed in some continuous phase or in which the solubilized active ingredient constitutes the continuous phase.

A variety of cream formulations (also known as soft solids or semi-solids) are known. Various of these cream formulations include a clay thickening agent, and an activator for such clay thickening agent. See, for example, U.S. Pat. No. 5,019,375 to Tanner, et. al.; and U.S. Pat. No. 4,526,780 to Marschner, et. al.

Other cream compositions contain a particulate thickening agent such as fumed silica. See U.S. Pat. No. 5,069,897 to Orr, et. al. and U.S. Pat. No. 4,937,069 to Shin et. al.

U.S. Pat. No. 5,102,656 to Kasat, the contents of which are incorporated herein by reference in their entirety, discloses a creamy, heterogeneous, anhydrous antiperspirant product containing, in percent by weight of the total weight of the composition, 30%–70% of a volatile silicone product as a carrier, 7–30% of a suitable gelling agent or agents, and about 12–30% of a physiologically acceptable antiperspirant agent. This patent discloses that the gelling agent can be any of a number of materials, including, for example, hydrogenated vegetable oil, hydrogenated castor oil, fatty acids, beeswax, paraffin wax, fatty alcohols, polyethylene and the like.

U.S. Pat. No. 4,331,653 to Brown, et. al. discloses a styptic composition which effectively curtails bleeding while administering a soothing sensation to an injured area, the composition being in the form of a stable lotion or cream and including specific amounts of a long-chain fatty acid, a wax filler, polyethylene glycol stearate, polyethylene glycol sorbitan beeswax, an acidic metallic salt (an agent to stem the flow of blood) and water. This patent discloses that the long-chain fatty acid, polyethylene glycol stearate and polyethylene glycol sorbitan beeswax are employed as emulsifiers or dispersing agents which promote the formation of a stable lotion or cream, these materials also being believed to be responsible for the soothing nature of the lotion or cream; and that the wax filler can be any of various wax products such as microcrystalline wax, paraffin wax, and, preferably, beeswax.

U.S. Pat. No. 4,948,584 to Brand, the contents of which are incorporated herein by reference in their entirety, discloses a modified beeswax, suitable for use in cosmetic preparations, which does not cause any crystallization in the fatty phase, the modified beeswax containing no or virtually no free acids. This patent discloses that the modified beeswax has self-emulsifying characteristics and has an outstanding dispersant action for solid substances. This patent discloses that the modified beeswax is capable of gelling fluid oils and other waxes (including synthetic triglycerides and lipophilic silicone oils), the viscosity of the oil being co-determining of the amount of beeswax to be used.

Notwithstanding all of the foregoing, it is still desired to provide a cosmetic composition (e.g., a solid cosmetic composition, including cream compositions) that is stable, substantially anhydrous and free of conventional gelling agents such as fatty alcohols and castor oil waxes, and which leaves substantially no visible (white) residue upon application and after drying. In particular, it is desirable to provide an antiperspirant cream composition that is stable, substantially anhydrous and free of conventional gelling agents, and which exhibits substantially no visible (white) residue upon application and after drying.

SUMMARY OF THE INVENTION

Accordingly, it is an object of the present invention to provide a cosmetic composition (for example, a solid cosmetic composition such as a cream composition or soft solid or semi-solid composition) which is stable, and which is substantially anhydrous, such composition packaged in a dispensing cannister, and a method of using such cosmetic composition.

It is a further object of the present invention to provide such cosmetic composition, which need not include conventional gelling agents such as fatty alcohols (e.g., stearyl alcohol) and castor oil waxes (e.g., hydrogenated castor oil).

It is a still further object of the present invention to provide such cosmetic composition, containing an active material selected from the group consisting of deodorant active materials, antiperspirant active materials, sunscreen materials, insect repellents and anti-fungal agents, which leaves substantially no visible (white) residue, such composition packaged in a dispensing cannister and a method of using such composition.

It is a still further object of the present invention to provide a cosmetic cream composition containing active cosmetic materials as discussed previously, and which does not contain conventional gelling agents, yet which is stable and efficacious, and a method of using such composition.

It is especially an object of the present invention to provide an antiperspirant composition (e.g., an antiperspirant cream composition) containing an antiperspirant active metal salt (for example, an antiperspirant active aluminum-containing salt), which composition is anhydrous and stable, contains no conventional gelling agents, and exhibits no visible (white) residue after application and after drying, such antiperspirant composition packaged in a dispensing cannister, and a method of using the composition.

The foregoing objects are achieved by the cosmetic composition of the present invention, containing, as a gelling agent in the composition, hexanediol-behenyl beeswax, the gelling agent containing hexanediol-behenyl beeswax being included in combination with volatile silicone materials and linear chain silicone materials in the composition. The linear chain silicone materials can be volatile or non-volatile. Thus, the cosmetic composition of the present invention includes volatile silicone material; linear chain silicone material; at least one gelling agent, this gelling agent being included in the composition in an amount to thicken the composition so as to provide a solid composition, the gelling agent including hexanediol-behenyl beeswax; and at least one active cosmetic material selected from the group consisting of deodorant active materials, antiperspirant active materials, sunscreen materials, insect repellents and anti-fungal agents. The active cosmetic material is to be included in the composition in an amount sufficient to have a functional effect; for example, where a sunscreen material is incorporated in the composition, a sufficient amount of the sunscreen material should be incorporated to provide a sunscreening effect.

As indicated previously, the gelling agent, which includes the hexanediol-behenyl beeswax, is included in the composition in an amount to thicken the composition, so as to provide a solid composition. For example, a cream composition can be provided by including a sufficient amount of gelling agent in the composition so as to thicken the composition to be a cream.

Illustratively, the gelling agent can consist only of the hexanediol-behenyl beeswax. However, the gelling agent need not be limited to only this beeswax, and can include mixtures of this beeswax with other gelling materials. Moreover, and further illustrating and not limiting the present invention, the hexanediol-behenyl beeswax can be included in the composition in an amount of 3%–25% by weight of the total weight of the composition.

Illustratively, the volatile silicone material included as part of the present composition can be a cyclomethicone, although the present invention is not limited to including a cyclomethicone as a volatile silicone material. The linear chain silicone material can include dimethicone and/or phenyl trimethicone, although the linear chain silicone material is not limited to these materials.

As a preferred composition of the present invention, the composition can include an antiperspirant active material (for example, an antiperspirant active metal salt, such as an antiperspirant active aluminum-containing salt) as the active cosmetic material. This antiperspirant active material can be in particulate form, suspended in the remainder of the composition. Antiperspirant active material can be included in the composition in an amount sufficient to reduce flow of perspiration when applied to the skin, such that the composition is an antiperspirant composition (such as an antiperspirant cream composition).

Alternatively, where the amount of antiperspirant active material included in the composition is not sufficient to reduce flow of perspiration, but is sufficient to reduce body malodor (for example, acting as a bacteriostat), the composition will constitute a deodorant composition, while not being an antiperspirant composition. Thus, incorporating such lesser amounts of antiperspirant active materials will still reduce body malodor and achieve an object of the present invention, and compositions including such lesser amounts are still within the scope of the present invention.

The compositions according to the present invention need not include conventional gelling agents such as fatty alcohols and/or castor oil waxes, and yet achieve a stable, substantially anhydrous gelled cosmetic composition. Moreover, the compositions of the present invention are efficacious; for example, when including antiperspirant active materials in the composition, the composition can contain sufficient antiperspirant active material to reduce flow of body perspiration, and achieve this result in a composition that does not leave a visible (white) residue after application or after drying.

Cosmetic compositions according to the present invention are easy to manufacture, being formed by mixing an active cosmetic material, the volatile and linear chain silicone materials and the gelling agent. After mixing to form the composition, the composition according to the present invention can be introduced into a dispensing container as known in the art. For example, where a cream composition is formed, this composition can be packaged in containers which have the appearance of a stick, but which dispense product through apertures in the top surface of the package. In use, the product is extruded from a reservoir within the package onto the top surface of the package, through these apertures, and the product on the top surface is applied (rubbed) on a desired location (for example, where the product is an antiperspirant product for application to axillary regions of the human body, the product on the top surface can be applied (rubbed) on the axillary regions of the human body), so as to deposit the product containing the active cosmetic material (for example, deodorant and/or antiperspirant active material).

By the present invention, a stable, substantially anhydrous, cosmetic composition can be provided, which leaves substantially no visible (white) residue on the skin after application and after drying of the deposited film, yet which is highly efficacious. By incorporating an antiperspirant active material in the composition, and incorporating an amount of gelling agent to form a cream, an antiperspirant cream composition can be provided which is efficacious and leaves substantially no visible residue, yet which does not require conventional gelling agents.

DETAILED DESCRIPTION OF THE INVENTION

While the present invention will be described in connection with specific and preferred embodiments, it is understood that it is not intended to limit the invention to those embodiments. To the contrary, it is intended that the present invention cover all alterations, modifications and equivalents as may be included within the spirit and scope of the invention as defined by the appended claims.

Throughout the present disclosure, the present invention is described primarily in connection with antiperspirant compositions, including antiperspirant cream compositions. However, the present invention is not limited to such compositions; for example, the composition according to the present invention can be a sunscreen composition. Depending on the active cosmetic ingredients included in the composition, the composition can be an insect repellent composition, a sunscreen composition, an anti-fungal composition, etc. As to various types of cosmetic compositions and active materials incorporated therein, applicable to the present invention, attention is directed to U.S. Pat. No. 4,322,440 to Yuhas, the contents of which are incorporated herein by reference in their entirety.

Throughout the present specification, "deodorant active materials" and "antiperspirant active materials" are discussed. Both types of materials contribute to reduction of body (for example, axillary) malodor. By reduction of body malodor is meant that, generally, there is less body malodor after application to a person's skin, as compared to a person's malodor without application of the composition. Such reduction can be due to a masking of the malodor, absorption and/or chemical reaction of the malodorous materials, reduction of the levels of the bacteria producing the malodorous materials, i.e. from perspiration, reduction of perspiration, etc. The antiperspirant materials, when utilized in appropriate amounts, primarily act to reduce malodor by reducing perspiration; the antiperspirant materials can also have a deodorant function, e.g., as an antimicrobial or bacteriostatic agent. The deodorant material does not substantially reduce perspiration, but reduces malodor in other ways, e.g., as fragrances masking the malodor or reducing the malodor intensity, as absorbents, as antimicrobial (bacteriostatic) agents, as agents chemically reacting with malodorous material, etc.

Throughout the present specification, where compositions are described as including or comprising specific components or materials, and where methods are described as including or comprising specific steps, it is contemplated by the inventors that the compositions and methods of the present invention also consist essentially of, or consist of, the recited components or materials, or the recited steps. Accordingly, throughout the present disclosure any described composition of the present invention can consist essentially of, or consist of, the recited components or materials, and any method can consist essentially of, or consist of, the recited steps.

The present invention contemplates a cosmetic composition (for example, a solid (solidified) cosmetic composition) containing (1) active cosmetic material selected from the group consisting of deodorant active materials, antiperspirant active materials, sunscreen materials, insect repellents and anti-fungal agents; (2) volatile silicone materials; (3) linear chain (that is, not cyclic) silicone materials; and (4) at least one gelling agent, the at least one gelling agent including hexanediol-behenyl beeswax.

The active cosmetic material is included in the composition in an amount sufficient to have a functional effect, such amounts being those conventionally utilized in the art. See, for example, the amounts described in the aforementioned U.S. Pat. No. 4,322,400 to Yuhas, the contents of which have previously been incorporated herein by reference in their entirety.

While the gelling agent can consist of the hexanediol-behenyl beeswax (that is the hexanediol-behenyl beeswax can be the only gelling agent incorporated in the composition), the gelling agent is not limited to this hexanediol-behenyl beeswax, and can include a mixture of this beeswax and other gelling materials. Generally, the gelling agent is included in the composition in an amount of 3–30%, preferably 5–20%, by weight, of the total weight of the composition. Preferably, the hexanediol-behenyl beeswax is included in the composition in an amount of 3–25% by weight of the total weight of the composition.

In the following will be set forth a description of hexanediol-behenyl beeswax. Hexanediol-behenyl beeswax is manufactured, for example, by Koster Keunen, Inc. (Watertown, Conn.), and is a modified beeswax wherein the free fatty acids have been subjected to transesterification. As manufactured by Koster Keunen, Inc., the hexanediol-behenyl beeswax is a solid amorphous material having a melting point in the range of 62°–68° C. and an acid value less than 2. This modified beeswax has a saponification value in the range of 80–90. The hexanediol-behenyl beeswax has a free fatty acid content of less than 1%, and fatty acid ester-type derivatives of around 11%. The modified beeswax includes 15% hydrocarbons, 14% complex ester and 60% mono-ester.

Koster Keunen, Inc. vends the hexanediol-behenyl beeswax as Beeswax Ester 103. This Beeswax Ester 103 provides gels of silicone oils which are non-greasy, non-occlusive, have high spreadability and compatibility, have a high oxidation resistance, are highly water repellent, achieve easy rub-out, and leave a soft feel and lubricity on the skin. These gels are a major factor in forming stable emulsions, and in many cases the production of non-granular, silky and thixotropic gels will lead to a luxurious feeling, high emolliency from an emulsion.

The Beeswax Ester 103 has 100% compatibility with various cyclomethicones, phenyl methicones, and dimethicones.

The beeswax derivatives of Koster Keunen, Inc., formed by transesterification, in general have the following formulating advantages: they gel highly polar oils; are an excellent moisturizer and emollient; provide water-resistance (act as a barrier); are highly compatible; can act as an emulsion stabilizer; can act as a pigment dispersant aid; are a stabilizer; and can also act as a film former. These materials are also known for their sunscreen enhancement. These beeswax derivatives have uses in creams, lotions, make-ups, anhydrous gels/lipsticks, and in hair care.

The volatile silicone material to be incorporated in the composition of the present invention can be selected from known volatile materials including cyclic and linear silicone materials, and mixtures thereof. Preferred volatile silicone materials are the cyclomethicones (e.g., cyclomethicone D4, D5 or D6). Other volatile silicones include the Dow Corning 200 Fluids 0.65CS, 1CS and 1.5CS, which are volatile dimethicones. Another volatile silicone material which can be incorporated in the composition of the present invention is caproyl trimethicone fluid (e.g., DC 2-1731). Illustratively, the volatile silicone material is included in the composition in an amount of 30–60%, preferably 35–55%, by weight, of the total weight of the composition.

The linear chain silicone material can include dimethicone and/or phenyl trimethicone, but the linear chain silicone materials are not limited to these. For example, dimethicone copolyol can also be included as a linear chain silicone material in compositions of the present invention. The linear chain silicone material can be volatile or non-volatile. For example, the various DC 200 Fluids (which are various dimethicones) can be used as the linear chain silicone material of compositions of the present invention. DC 200 Fluids with viscosity from 0.65CS to 1.5CS are considered to be volatile while those with viscosity greater than 1.5CS are considered to be non-volatile, and each can be used as the linear chain silicone in the present invention.

Illustratively, and not to limit the present invention, the linear chain silicone material can be incorporated in the composition of the present invention in an amount of 5–40%, preferably 10–30%, by weight, of the total weight of the composition. Dimethicone copolyol can be incorporated as a linear chain silicone material in an amount of 0.1–10%, preferably 0.5–6.0%, by weight, of the total weight of the composition.

As indicated previously, the active cosmetic material can be any of various active materials, including (but not limited to) deodorant active materials and antiperspirant active materials.

Where the composition is an antiperspirant composition, various antiperspirant active materials can be incorporated in the composition. These include, by way of example (and not of a limiting nature), aluminum chlorohydrate, aluminum chloride, aluminum sesquichlorohydrate, zirconyl hydroxychloride, aluminum-zirconium hydroxychlorides, aluminum-zirconium glycine complex (e.g., aluminum-zirconium tetrachlorohydrex-gly), etc. The aluminum-type materials can be commonly referred to as antiperspirant active aluminum salts. Generally, the foregoing metal-containing antiperspirant active materials are antiperspirant active metal salts. The compositions according to the present invention need not include aluminum-containing metal salts, and can include other antiperspirant active metal salts. Generally, Category I active antiperspirant ingredients listed in the Food and Drug Administration's Monograph on antiperspirant drug products for over-the-counter use (Oct. 10, 1973) can be used. In addition, any new drug, not listed in the Monograph, such as aluminum nitratohydrate and its combination with zirconyl hydroxychlorides and nitrides, or aluminum-stannous chlorohydrates, can be incorporated as an antiperspirant active ingredient in antiperspirant compositions according to the present invention.

The antiperspirant active material, desirably, is included as a particulate suspended in the composition of the present invention, in amounts up to, e.g., 30% by weight of the total weight of the composition. This is an illustrative amount and is not limiting of the present invention. As an illustrative amount, and not to be limiting, the composition could include at least 0.1% by weight antiperspirant active material, of the total weight of the composition; however, at low amounts the material may not reduce perspiration (for example, it may act as a deodorant active material, such as an antimicrobial or a bacteriostatic agent rather than to reduce perspiration). Illustratively, the composition should include at least 12% by weight, of the total weight of the composition, of the antiperspirant active material, in order for the composition to act as an antiperspirant composition (to reduce flow of perspiration from a person).

Whether the composition is a deodorant composition or a antiperspirant/deodorant composition, appropriate deodorant active materials can be incorporated in the composition, so as to provide deodorant active materials for combatting body malodor. For example, a deodorant fragrance and/or antimicrobial agent (bacteriostat) can be incorporated. A fragrance would, illustratively, be incorporated in an amount of 0.5%–3.0% by weight, of the total weight of the composition; the antimicrobial/bacteriostatic material, such as Triclosan, would preferably and illustratively be included in an amount of from 0.1%–0.5% by weight, of the total weight of the composition.

Compositions according to the present invention can include other ingredients conventionally incorporated in cosmetic compositions, including (but not limited to) perfumes, cosmetic powders, colorants and emulsifiers. As to various other ingredients that can be included, attention is directed to the optional components, such as the colorants, perfumes and fillers, described in the following U.S. patents: U.S. Pat. No. 5,019,375 to Tanner, et. al. (the contents of which are incorporated herein by reference in their entirety); U.S. Pat. No. 4,937,069 to Shin (the contents of which are incorporated herein by reference in their entirety); and U.S. Pat. No. 5,102,656 to Kasat (the contents of which have been previously incorporated herein by reference in their entirety).

Compositions according to the present invention can be made by mixing the active cosmetic material, the volatile silicone material, the linear chain silicone material and the gelling agent in liquid form, to form a mixture. The mixture can be introduced into dispensing canisters (containers), as with conventional solid compositions (for example, conventional cream compositions). Where the composition is a cream (soft solid or semi-solid, for example), these dispensing canisters can be canisters which have a top surface with slots therein, the composition being extruded onto the top surface from a reservoir in the canister, and then applied (for example, rubbed on the skin) from the top surface so as to deposit a film of the product on the skin. See U.S. Pat. No. 5,540,361 to Fattori, issued Jul. 30, 1996, the contents of which are incorporated herein by reference in their entirety, for a dispensing container which can be used to dispense cream (semi-solid or soft solid) composition of the present invention.

As a specific illustration of the manufacturing process (which is not to be limiting), initially the hexanediol-behenyl beeswax is heated and melted at about 60°–75° C. Then the linear chain silicone material, volatile silicone material, active cosmetic material (e.g., antiperspirant active material), and the rest of the composition components are blended and mixed into the molten beeswax, so as to form a uniform mixture. The mixture is then cooled to around 54° C., and poured into dispensing canisters.

Illustratively, where the composition is an antiperspirant composition containing an antiperspirant active material for reducing perspiration in axillary regions, in use the composition is extruded from inside the dispensing canister through the slots onto the top surface of the dispensing canister, and from there is applied (rubbed) on the skin in the axillary regions, so as to deposit sufficient antiperspirant active material (and, if present, sufficient deodorant active material) so as to reduce perspiration and body malodor originating in axillary regions of the human body.

In the following, specific examples of compositions within the scope of the present invention are set forth. These specific examples are illustrative of the present invention, and are not limiting. In these examples, the amounts of the components are in weight percent of the total weight of the composition. In these examples, as well as throughout the specification, various names utilized are the CTFA (Cosmetic, Toiletry and Fragrance Association, Inc.) names, as set forth in the CTFA International Cosmetic Ingredient Dictionary (4th Ed. 1991).

EXAMPLE 1

| Ingredient | % |
| --- | --- |
| HEXANEDIOL-BEHENYL BEESWAX | 15.00 |
| AL-ZR TETRACHLOROHYDREX-GLY | 21.50 |
| PHENYL TRIMETHICONE (Dow Corning 556 Fluid) | 38.50 |
| DIMETHICONE, .65CS | 25.00 |
| TOTAL | 100.00 |

EXAMPLE 2

| Ingredient | % |
| --- | --- |
| HEXANEDIOL-BEHENYL BEESWAX | 5.00 |
| AL-ZR TETRACHLOROHYDREX-GLY | 25.00 |

-continued

| Ingredient | % |
| --- | --- |
| DIMETHICONE, 50CS | 25.00 |
| CYCLOMETHICONE (Dow Corning 245 Fluid) | 45.00 |
| TOTAL | 100.00 |

EXAMPLE 3

| Ingredient | % |
| --- | --- |
| HEXANEDIOL-BEHENYL BEESWAX | 5.00 |
| AL-ZR TETRACHLOROHYDREX-GLY | 25.00 |
| DIMETHICONE, 50CS | 25.00 |
| CYCLOMETHICONE (Dow Corning 245 Fluid) | 44.00 |
| PROPYLENE CARBONATE | 1.00 |
| TOTAL | 100.00 |

EXAMPLE 4

| Ingredient | % |
| --- | --- |
| HEXANEDIOL-BEHENYL BEESWAX | 5.00 |
| AL-ZR TETRACHLOROHYDREX-GLY | 25.00 |
| CYCLOMETHICONE (Dow Corning 244 Fluid) | 45.00 |
| DIMETHICONE, 50CS | 25.00 |
| TOTAL | 100.00 |

EXAMPLE 5

| Ingredient | % |
| --- | --- |
| HEXANEDIOL-BEHENYL BEESWAX | 6.00 |
| AL-ZR TETRACHLOROHYDREX-GLY | 25.00 |
| DIMETHICONE, 50CS | 12.00 |
| CYCLOMETHICONE (Dow Corning 245 Fluid) | 54.50 |
| ALUMINUM STARCH OCTENYL-SUCCINATE | 2.00 |
| FRAGRANCE | 0.50 |
| TOTAL | 100.00 |

EXAMPLE 6

| Ingredient | % |
| --- | --- |
| HEXANEDIOL-BEHENYL BEESWAX | 5.00 |
| AL-ZR TETRACHLOROHYDREX-GLY | 25.00 |
| DIMETHICONE, 50CS | 12.00 |
| CYCLOMETHICONE (DOW Corning 245 Fluid) | 54.50 |
| POLYETHYLENE | 3.00 |
| FRAGRANCE | 0.50 |
| TOTAL | 100.00 |

EXAMPLE 7

| Ingredient | % |
| --- | --- |
| HEXANEDIOL-BEHENYL BEESWAX | 5.00 |
| AL-ZR TETRACHLOROHYDREX-GLY | 25.00 |

-continued

| Ingredient | % |
| --- | --- |
| DIMETHICONE, 50CS | 25.00 |
| CYCLOMETHICONE (Dow Corning 244 Fluid) | 43.50 |
| DIMETHICONE COPOLYOL & CYCLOMETHICONE (Dow Corning 3225C Formulation Aid) | 1.00 |
| FRAGRANCE | 0.50 |
| TOTAL | 100.00 |

EXAMPLE 8

| Ingredient | % |
| --- | --- |
| HEXANEDIOL-BEHENYL BEESWAX | 5.00 |
| AL-ZR TETRACHLOROHYDREX-GLY | 25.00 |
| DIMETHICONE, 50CS | 21.00 |
| CYCLOMETHICONE (Dow Corning 244 Fluid) | 43.50 |
| DIMETHICONE COPOLYOL (Dow Corning 2501 Fluid) | 5.00 |
| FRAGRANCE | 0.50 |
| TOTAL | 100.00 |

Thus, according to the present invention, a cosmetic composition (for example, a solid cosmetic composition, such as a cream composition) containing an active cosmetic material (including, but not limited to deodorant and antiperspirant active materials) can be provided, which composition is efficacious and exhibits no visible (white) residue (either upon application or after drying). The composition does not require any conventional gelling agent such as fatty alcohols or castor oil waxes. Moreover, the composition does not require clay or particulate thickening agents, and is anhydrous. Furthermore, the active ingredient (e.g., an antiperspirant active material) can be provided in particulate form, suspended in an anhydrous composition.

The subject matter of this application is related to the subject matter described in the application entitled "Non-Aqueous Antiperspirant Composition", naming Makarand Shevade, Robert Bianchini and Francis J. Bala, Jr. as inventors (attorney docket no.: 851.34496X00), filed concurrently herewith, the contents of which are incorporated herein by reference in their entirety.

While we have shown and described several embodiments in accordance with present invention, it is understood that the same is not limited thereto, but is susceptible to numerous changes and modifications known to one having ordinary skill in the art, and we therefore do not wish to be limited to the details shown and described herein, but intend to cover all such modifications that are encompassed by the scope of the appended claims.

What is claimed is:

1. Solid antiperspirant composition, for application to a human, comprising:
    (a) at least one active antiperspirant material, in an amount sufficient to have an antiperspirant effect;
    (b) volatile silicone material;
    (c) linear chain silicone material; and
    (d) at least one gelling agent, the at least one gelling agent being included in the composition in an amount sufficient to thicken the composition so as to provide a solid composition, the at least one gelling agent including hexanediol-behenyl beeswax, the hexanediol-behenyl beeswax being included in the composition in an amount of 3%–25% by weight of the total weight of the composition.

2. The solid antiperspirant composition according to claim 1, wherein the at least one gelling agent consists of said hexanediol-behenyl beeswax.

3. The solid antiperspirant composition according to claim 1, wherein the volatile silicone material includes cyclomethicone, and the linear chain silicone material includes at least one of dimethicone and phenyl trimethicone.

4. The solid antiperspirant composition according to claim 3, wherein the at least one gelling agent is included in the composition in an amount so as to provide a cream composition.

5. The solid antiperspirant composition according to claim 1, wherein the at least one gelling agent is included in the composition in an amount so as to provide a cream composition.

* * * * *